United States Patent [19]

Knazek et al.

[11] 4,184,922
[45] Jan. 22, 1980

[54] DUAL CIRCUIT, WOVEN ARTIFICIAL CAPILLARY BUNDLE FOR CELL CULTURE

[75] Inventors: Richard A. Knazek; Pietro M. Gullino, both of Bethesda, Md.; David S. Frankel, Newark, Del.

[73] Assignee: The Government of the United States, Washington, D.C.

[21] Appl. No.: 850,810

[22] Filed: Nov. 11, 1977

[51] Int. Cl.² ............................ C12K 1/10; C12K 9/00
[52] U.S. Cl. ...................................... 435/284; 435/241; 435/283; 435/1
[58] Field of Search ........................................ 195/127

[56] References Cited

U.S. PATENT DOCUMENTS

| 3,732,149 | 5/1973 | Santero | 195/127 X |
| 3,740,321 | 6/1973 | Pagano et al. | 195/127 |
| 3,821,087 | 6/1974 | Knazek et al. | 195/127 |
| 3,827,943 | 8/1974 | Mann | 195/127 |
| 3,843,454 | 10/1974 | Weiss | 195/127 |
| 3,847,749 | 11/1974 | Smith et al. | 195/127 |
| 3,853,712 | 12/1974 | House et al. | 195/127 |
| 3,883,393 | 5/1975 | Knazek et al. | 195/1.8 |

OTHER PUBLICATIONS

Michael Russ; Mass Transfer by Connection and Diffusion in an Artificial Capillary System; Graduate Thesis, Jun. 1976.

Primary Examiner—Raymond N. Jones
Assistant Examiner—Robert J. Warden
Attorney, Agent, or Firm—Holman & Stern

[57] ABSTRACT

An artificial capillary cell culture device having two separate perfusion circuits, and with the ultrafiltration fibers of the two circuits being woven into a single bundle, is disclosed. The present device provides a matrix for high density growth of cultured cells in a continuous perfusion system. The device is particularly well adapted for the use of pressure differences between perfusion circuits, such as in the simulation of lymphatic drainage.

2 Claims, 4 Drawing Figures

DUAL CIRCUIT, WOVEN ARTIFICIAL CAPILLARY BUNDLE FOR CELL CULTURE

BACKGROUND AND SUMMARY OF THE INVENTION

The present invention is concerned with an artificial capillary cell culture device. More particularly, the present invention relates to an artificial capillary cell culture device having improved features which include the incorporation into a single bundle of ultrafiltration fibers connected to two separate perfusion circuits and the interweaving of fibers to maintain intimate contact. The artificial capillary device of the present invention provides a matrix for high density growth of cultured cells in a continuous perfusion system.

Previous artificial capillary cell culture devices have included the device described in U.S. Pat. No. 3,883,393 to Knazek, et al., in which there is provided a bundle of unwoven hollow fibers connected to a single perfusion circuit. In such devices, in which the fibers are laid out parallel to one another during construction of the bundle, there are three main problems which are inherent. One problem is that the fibers may splay apart from one another when the bundle is sealed in the shell, increasing the possibility that cells between fibers may be anoxic, thus preventing the formation of a continuous tissue-like cell mass on the fiber bundle. A second main problem resides in the fact that the fibers may dry and contract following humidified ethylene oxide sterilization of the device, one result being that breakage may occur more easily in individual fibers. A third problem concerns distribution of nutrients which occurs simply by diffusion in the previous device.

By the present invention, there is provided an artificial capillary cell culture device which has overcome the difficulties described in connection with previous cell culture devices such as that of U.S. Pat. No. 3,883,393. The cell culture device of the present invention has features which include the incorporation into a single woven bundle of ultrafiltration fibers, with a portion of the fibers being connected to one perfusion circuit and the remaining fibers being connected to a second perfusion circuit. A difference in pressure between the two circuits produces convective currents of perfusate within the extracapillary space and improves nutrient distribution. Thus the present device is provided with two separate perfusion circuits which feed a single culture unit, but with the fibers associated with the separate circuits being in intimate contact with one another in a woven configuration. The present construction permits observation of mass transfer of chemical species from one perfusion circuit into another through the cell mass. In addition, the present device provides for induction of fluid filtration between perfusion circuits to simulate processes such as lymphatic drainage of the cell mass.

The woven construction of the present fiber bundle results in a fiber bundle which is coherent and yet compliant, with the fibers from the separate circuits being in intimate contact. In addition, while the weaving of the fiber bundle provides structural strength, at the same time the bundle is sufficiently flexible to absorb possible contractions or displacements caused by the imposition of fluid pressure differences required to employ the device in processes such as inducing simulated lymphatic drainage.

BRIEF DESCRIPTION OF THE DRAWINGS

The advantages and features of the present invention will be more fully understood from the following description of the preferred embodiments, taken in conjunction with the accompanying drawings, wherein.

DESCRIPTION OF THE PREFERRED EMBODIMENTS

Figure 1:
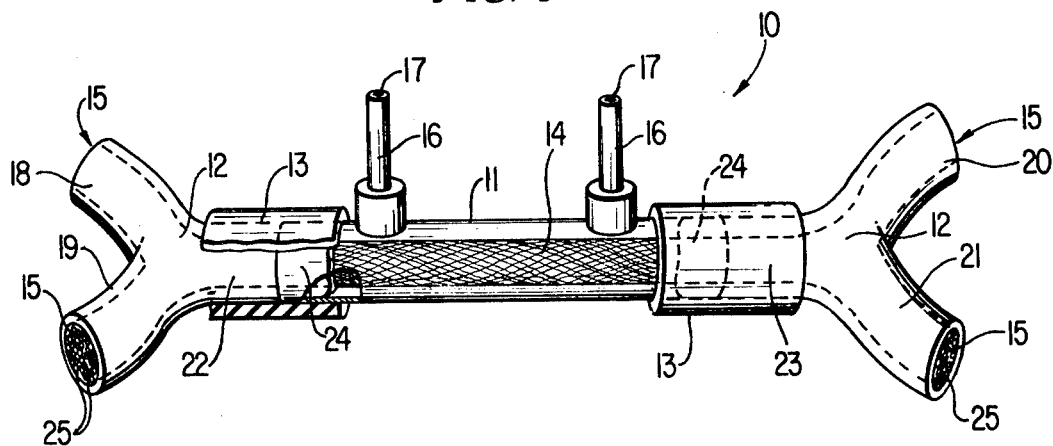
FIG. 1 is a perspective view of a cell culture unit of the present invention.
Figure 2:
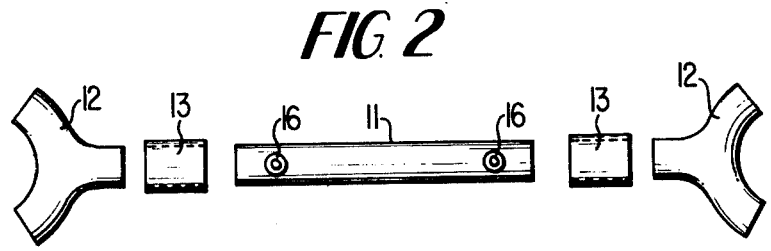
FIG. 2 is an exploded perspective view of the cell culture unit of FIG. 1, showing various components thereof, prior to assembly and insertion of the woven capillary fiber bundle.

In the embodiment of the invention as shown in FIGS. 1 and 2, a cell culture unit (CCU) 10 is provided, having a shell member 11 connected at each end to a Y-connector endpiece 12 by means of connecting sleeves 13. A woven capillary fiber bundle 14 extends the length of the shell 11 with portions of the bundle 14 extending through to the ends 15 of the endpieces 12. A pair of inoculation ports 16 of conventional construction are provided to allow access to the extracapillary space through holes 17 having a diameter such as, for example, about 55 mil.

The shell member 11 is preferably of a clear, durable material such as polycarbonate to provide visibility of the woven bundle 14 within the shell 11. The dimensions of the shell 11 may be, for example, a length of 5 cm with $\frac{1}{4}''$ I.D. and $\frac{3}{8}''$ O.D.

The endpieces 12 may be of a material such as standard Pyrex glass Y-connectors having dimensions such as, for example, 3/16" I.D. and 5/16" O.D., and cut down to yield a pair of arms of about 16 mm in length. Thus there are provided a pair of arms 18, 19 at one end, and a pair of arms 20, 21 at the opposite end of the unit 10. The base portions 22, 23 of the endpieces 12 may be about 13 mm in length.

The connecting sleeves 13 may be formed of a material such as a Silastic tubing, a Dow-Corning silicone rubber medical grade tubing, of a length of about 17–20 mm with $\frac{1}{4}''$ I.D. and $\frac{3}{8}''$ O.D. These sleeves 13 are employed to hold the endpieces 12 butted against the shell 11.

As described hereinafter, potting material 24 is employed to fill the endpieces 12 and intrude approximately 5 mm into the shell 11 at each end. The potting material 24 may be any suitable composition employed in the art. One composition which has been employed with good results includes 60 wt.% General Electric Co. RTV (Room temperature vulcanizing)—11 silicone rubber and 40 wt.% Dow-Corning 360 medical fluid. This mixture is catalyzed with stannous octoate and aspirated into the endpieces. When the potting material 24 is trimmed away from the outer ends 15 of the endpieces 12, the capillary lumens 25 of the fibers making up the bundle 14 are revealed.

When the capillary fibers have been installed within the unit 10 as described in detail hereinafter, one set of capillaries, such as about 50 capillaries, is potted through arms 19 and 21 while a second set of about 50 capillaries is potted through arms 18 and 20. Thus one perfusion circuit (not shown) may be employed to pump fluid from arm 19 to arm 21 through one set of capillaries while a second perfusion circuit (not shown) pumps fluid from arm 18 to arm 20.

Figure 3:
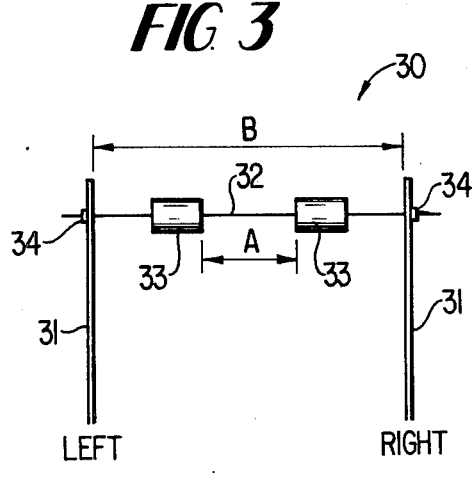
FIG. 3 is a front elevational view of the fiber bundle jig used to weave the fibers.
Figure 4:
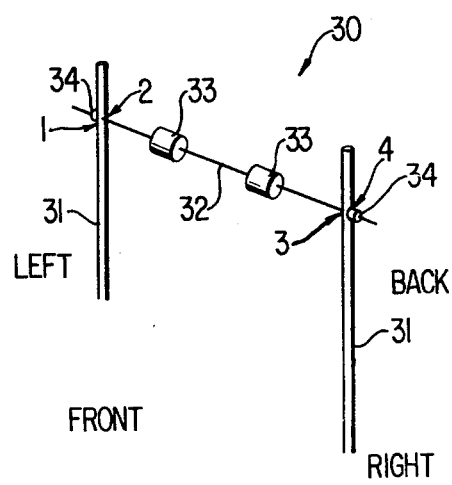
FIG. 4 is a perspective view of the fiber bundle jig of FIG. 3, showing the fiber attachment points.

In FIGS. 3 and 4 there is shown the fiber bundle jig 30 employed in producing the woven fiber bundle 14. The jig 30 includes a pair of rods 31 clamped in vertical position on any suitable base (not shown) and with holes drilled in the upper ends of the rods 31 to accomodate a stainless steel wire mandrel 32. The rods 31 may be formed, for example, of polycarbonate material having a diameter of about ½", while the mandrel 32 has a diameter of about 1/16". A pair of spreader collars 33 are installed on the mandrel 32 as shown in FIGS. 3 and 4. These spreader collars 33 may be formed, for example, of nested Silastic tubing sections with ⅛" O.D.×1/16" I.D. tubing on the mandrel 32, then a 2/10" O.D.×1/10" I.D. tubing over the 1/16" tubing and finally a 5/16" O.D.×3/16" I.D. tubing over the 1/10" tubing. The distance "A" between spreader collars 33 may be about 4.8 cm, for example, with the distance "B" between vertical rods 31 being about 13.2 cm. External slip-on collars 34 of a material such as 1/16" I.D. Silastic tubing, are slipped over the mandrel 32 on each end and snugged up adjacent the outer sides of the rods 31.

In the perspective view of FIG. 4, there are shown the four fiber attachment points 1,2,3,4 on the rods 31. Point 1 (left front) and point 2 (left back) and correspondingly, point 3 (right front) and point 4 (right back), are diametrically opposed sites on the upright rods 31 where the mandrel 32 passes through.

The fibers employed in making up the bundle 14 may be any suitable hollow ultrafiltration fibers, such as those made by the Amicon Corporation of Lexington, Mass. Such semi-permeable fiber materials are further described in U.S. Pat. No. 3,883,393 which is incorporated herein by reference.

In preparing the woven fiber bundle 14 of the present invention, a swatch of double-sided tape is applied to each of the four fiber attachment sites 1,2,3 and 4 on the uprights 31 of the bundling jig 30. The fibers are applied one at a time to the bundle, and the count of fibers is kept on a hand tally counter or other suitable means. A fifteen-centimeter length of fiber is cut from a spool of fiber. One end is secured to the tape swatch at position 3. Next, the fiber is passed to position 2, and two turns are taken around the mandrel 32 in a clockwise sense (reference point—looking from the right upright along the mandrel 32 to the left upright) before the fiber is secured to the tape swatch at position 2. This process is repeated for a total of five fibers. Then a fiber is attached to position 1 and passed to position 4, and two turns are wound counterclockwise around the mandrel 32 enroute. Repeat this tack until a total of ten fibers have been applied. Then, return to the 3-to-2 tack for another five fibers. After every five fibers, switch tacks. Also, at each multiple of eleven fibers, the winding sense is reversed. In addition, the winding sense for the 1-to-4 tack is always opposite to that for the previous 3-to-2 tack, and vice versa. Finally, after sixty fibers have been applied, the number of turns is reduced to one. A total of one hundred fibers is bundled. It is advantageous to apply fresh tape swatches to the attachment sites after every twenty fibers.

A tabulation of this bundling procedure follows:

TABLE 1

| Tack | Fiber Numbers | Number of Turns Wrapped Around Mandrel |
|---|---|---|
| (origin-to-destination) | | |
| 3-to-2 | 1–5 | 2 |
| 1-to-4 | 6–10 | 2 |
| 3-to-2 | 11–15 | 2 |
| 1-to-4 | 16–20 | 2 |
| | apply fresh tape swatches | |
| 3-to-2 | 21–25 | 2 |
| 1-to-4 | 26–30 | 2 |
| 3-to-2 | 31–35 | 2 |
| 1-to-4 | 36–40 | 2 |
| | apply fresh tape swatches | |
| 3-to-2 | 41–45 | 2 |
| 1-to-4 | 46–50 | 2 |
| 3-to-2 | 51–55 | 2 |
| 1-to-4 | 56–60 | 2 |
| | apply fresh tape swatches | |
| 3-to-2 | 61–65 | 1 |
| 1-to-4 | 66–70 | 1 |
| 3-to-2 | 71–75 | 1 |
| 1-to-4 | 76–80 | 1 |
| | apply fresh tape swatches | |
| 3-to-2 | 81–85 | 1 |
| 1-to-4 | 86–90 | 1 |
| 3-to-2 | 91–95 | 1 |
| 1-to-4 | 96–100 | 1 |

A tabulation of the winding sense of the successive fibers is as follows:

Table 2

| FIBER NUMBERS | WINDING SENSE (looking down mandrel from right upright toward left upright) |
|---|---|
| 1–5 | CW |
| 6–10 | CCW |
| 11 | CW |
| 12–15 | CCW |
| 16–20 | CW |
| 21–22 | CCW |
| 23–25 | CW |
| 26–30 | CCW |
| 31–33 | CW |
| 34–35 | CCW |
| 36–40 | CW |
| 41–44 | CCW |
| 45 | CW |
| 46–50 | CCW |
| 51–55 | CW |
| 56–60 | CW |
| 61–65 | CCW |
| 66 | CW |
| 67–70 | CCW |
| 71–75 | CW |
| 76–77 | CCW |
| 78–80 | CW |
| 81–85 | CCW |
| 86–88 | CW |
| 89–90 | CCW |
| 91–95 | CW |
| 96–100 | CCW |

REMOVAL OF FIBER BUNDLE FROM JIG

The following steps should be carried out when removing the fiber bundle 14 from the jig 30:

1. Loosely apply thread ties in two locations, both one-half cm. and two cm. from the points of attachment at 1,2, 3, and 4. Use one color thread at 1 and 4, and a second color at 2 and 3 to distinguish the two separate fiber bundles. The thread tie close to the fiber attachment site will later serve to tightly bunch the fibers together; the second tie is a security measure to group fibers together in the event that some fibers escape the primary tie when the fibers are severed from the tape attachment. The ties should be loose slipknots which can later be slipped off the fiber bundle without crimping the fibers.

2. Carefully sever fibers from the points of attachment to tape swatches using a razor blade or similar means. Leave no tape clinging to fiber ends.

3. Use clean, dry thumb and forefinger to smooth bundle from spreader collar 33 to cut ends into a compact bundle of parallel fibers. In so doing, there should be no grossly loose or bowed-out fibers which would be susceptible to breakage when the bundle is later pulled into the shell 11. Tighten the ties nearest the bundle ends after positioning the ties as near the ends as possible while still encircling all fibers in that bundle. Firmly knot these end ties at one end only, i.e., at 1 and 2, or 3 and 4. If fibers escape the primary end ties, slide the secondary loose ties into the appropriate position and tighten.

4. Remove the tape swatches from the uprights 31. Remove external slip-on collars 34 from the mandrel 32. Remove the mandrel-bundle assembly from the jig 30 by sliding the uprights 31 apart. Place the mandrel-bundle assembly on a clean, dry working surface.

5. Apply appropriately colored thread leaders 20 cm. in length to the two bundle ends which were previously firmly knotted (as per step 3). These leaders should be tightly knotted in the same position as the primary end ties, and tied such that a long leader extends from one side of the knot.

6. Trim the fiber bundle ends from step 5 to within two mm. of the end tie. Trim the loose ends of the ties, except the two long leads, as close as possible to the knots. Remove the loose, secondary ties with forceps, being careful not to damage any fibers. The primary and secondary ties must remain in position at the other end of the bundle.

7. Use forceps or similar means to carefully remove the nested spreader collar 33 from the mandrel 32 nearest the bundle end prepared as in steps 5 and 6. Then grasp the two long leads between the fingers of the same hand and slowly ease the bundle 14 off the mandrel 32, evenly distributing tension between the two leads. Remount the spreader 33 and external collars 34 on the mandrel 32.

INSERTION OF FIBER BUNDLE INTO SHELL

The steps employed in inserting the fiber bundle 14 into the shell 11 are as follows:

1. Slip the two Silastic connecting sleeves 13 onto the ends of the CCU shell 11. Slip a dual-circuit endpiece 12 into the connecting sleeve 13 at one end of the shell 11 so that the ends of the shell 11 and endpiece 12 are held tightly together. With the endpiece 12 lying flat on the surface, the inoculation ports 16 should point vertically upward.

2. Thread the two long leads from the bundle 14 into the end of the shell 11 without the endpiece. The object is to have one lead projecting from one port of the connected endpiece 12 and the second lead projecting from the second port. The leads should not cross over one another within the shell 11. 3. Take up tension on the long leads by gently pulling on the projecting ends. The two ends of the bundle 14 should be simultaneously pulled into the shell 11 through the rubber connecting sleeve 13. It may be necessary to squeeze together the two ends with thumb and forefinger to ensure this. Then, very gently draw the bundle 14 into the shell 11, pulling the two leads so that the two ends travel at the same speed, until the ends project out of their respective endpiece ports about one cm. It is imperative that no fibers be crimped and broken during this process.

4. Some rearrangements must be made at the end of the bundle 14 which has not yet been fed through an endpiece. It is necessary to incorporate another one-half twist in this end of the bundle, following the "natural" twist in the body of the bundle so that the two ends of each of the separate bundled circuits lie on the same side of the CCU shell 11, rather than being diagonally opposed as on the fiber bundle jig 30. This is accomplished by positioning fiber bundle ends tied with the same color directly opposite one another.

5. To prevent fiber breakage during installation of the second endpiece 12 following incorporation of the extra half-twist, it is necessary to re-tie the fiber bundle ends at this end of the bundle 14. Working on one bundle at a time, check the orientation of the ends as per step 4. Remove the primary end tie carefully with forceps. Using clean, dry thumb and forefinger, smooth the fiber bundle into a compact form, with no protruding fibers, by gently stroking the bundle from the connecting sleeve 13 toward the bundle end. The loose, secondary tie is slipped gradually toward the bundle end and tightened when the bundle is satisfactorily coherent. Then, a ten cm. lead of appropriate color is knotted onto the bundle end to be used in guiding the bundle 14 into the second endpiece 12. The fiber bundle end is then trimmed to within 2 mm of the end tie.

6. Finally, thread the two leads into the second endpiece 12 and out separate ports. Carefully draw the two bundle ends into the common entrance simultaneously, being careful not to pull the bundle ends at the other end of the shell 11, back into the shell 11. Gently work the endpiece butt into the connecting sleeve 13, adjusting bundle position by means of the end leads so that no fibers are crimped and broken. Carefully push the endpiece 12 into the connecting sleeve 13 until the sleeve 13 holds the shell 11 and endpiece 12 tightly together. Adjust bundle position so that roughly equal lengths of fiber bundle protrude from the connector at each end. Check that bundle ends of the same color are directly, rather than diagonally, opposed.

POTTING THE CELL CULTURE UNIT

The steps to be carried out in potting the cell culture unit 10 are as follows:

1. Make new tight ties (the color of thread is now irrelevant) at all four bundle ends about 3 mm from the ends of the endpieces 12. Clip off excess bundle length about 4 mm away from these ties. Use a soldering iron to melt down the bundle ends back to the ties, thus sealing all fiber lumens for the potting process. Trim loose ends of ties flush.

2. Prepare a well-mixed mixture of a potting composition such as 24 gm. General Electric RTV-11 silicone rubber and 16 gm. Dow-Corning 360 Medical Fluid. This amount will pot fifteen headers (four per CCU).

3. Take a 20 cm. length of $\frac{1}{4}'' \times \frac{3}{8}''$ O.D. Silastic tubing and carefully slip one end over each header at one end of the CCU 10. The unit can be suspended at the proper height for potting by passing a string through the loop provided by this tubing.

4. Seal off a third header by slipping a 3 cm. length of ¼" I.D.×⅜" O.D. Silastic tubing over the header and applying a pinch clamp to the open end of the tubing. To seal the injection port closer to the end sealed with the tubing loop, slip on a 7 cm. length of 1/16" I.D. Silastic tubing with a tightly knotted end. A 65 cm. length of 1/16" I.D. Silastic is slipped over the second inoculation port 16 (the port closer to the header to be potted), and it is provided with a pinch clamp. Mouth suction should be applied to this tube to draw up potting composition 24 into the open header.

5. The CCU 10 is suspended so that the open header is perpendicular to and from 6 mm from the benchtop. A syringe (without needle) may be used to draw up and dispense 3 ml of potting mixture 24 into a disposable plastic 3 ml titration cup.

6. One drop of stannous octoate catalyst (General Electric Co.) is added to the 3 ml of potting mixture 24, which is then thoroughly mixed with the tip of a Pasteur pipette (10 sec) and then positioned so that the opening of the header is submerged to one-half the depth of the mixture 24. Mouth suction is slowly applied to the suction tubing to draw the potting material 24 up to the level of the bifurcation of the glass header. The suction tubing is then clamped off and the mixture is allowed to take its initial set (5–10 min.). This step should be performed quickly, since one drop of catalyst will rapidly render 3 ml of RTV composition gummy.

7. To pot the remaining three headers, follow a similar procedure, i.e., place clamped tubing over un-potted headers and suspend the open header to be potted in a titration cup containing 3 ml of freshly-catalyzed RTV rubber.

In carrying out this procedure, it should be noted that, at each end of the CCU:
 (a) The RTV in the first header to be potted is drawn up only to the bifurcation of the header, so that the main body of the endpiece doesn't seal off and prevent potting of the second header; and
 (b) The RTV in the second header is drawn up about 5 mm past the end of the main polycarbonate shell 11, but caution must be used to avoid applying too much suction, which may cause clogging of an injection port with RTV, or "wicking" of RTV up into the active region of the bundle 14.

8. After four hours of curing at room temperature, the titration cups are slit away from the rubber plugs to allow greater air access for curing the rubber. After 48 hours of curing, the rubber plugs are trimmed down and finally cut flush with the end of the header with a single slash of a sharp razor blade, revealing the open lumens 25 of the fibers.

The dual circuit, woven artificial capillary bundle has been successfully used to culture dense masses of $GH_3$ rat pituitary tumor cells (MtTW/5) and to quantify mass transport parameters for diffusion and convection of non-metabolite species through the cell mass by applying a differential pressure between the two circuits of about 300 mm Hg. In the culture of cells, the present device may be employed in a conventional manner, with cell suspension medium and cells to be cultured being passed into the shell unit 11 through inoculation ports 16. General procedures in this regard are outlined in U.S. Pat. No. 3,883,393. Also, the specific type of perfusion circuits to be employed will depend upon the particular use of the device. One such perfusion circuit which may be employed in both the circuits of the present device is that described in U.S. Pat. No. 3,883,393.

The cell culture device of the present invention may be advantageously employed in the simulation of flow or drainage through lymphatic channels. It is known that the factors which determine the rate and composition of lymph flow in humans and other animals include such factors as capillary pressure and tissue pressure. Other factors which are also important include plasma colloid osmotic pressure, tissue colloid osmotic pressure, total extracellular fluid volume and permeability of the capillaries. The general physiology of the lymphatic system is described, for example, by A. C. Guyton, *Textbook of Medical Physiology*, 2d. Edition, published by W. B. Saunders Co., Philadelphia, Pa., pp. 52–71, incorporated herein by reference.

Thus, considering the flow system which exists in the body between the capillaries and the lymphatic channels, with the interstitial spaces or tissues interposed therebetween, an analogy can be seen between this system and the cell culture device of the present invention, in which there are provided two separate perfusion circuits, one of which may represent the capillaries and the other the lymphatic channels and with the extracapillary space outside of the fibers representing the interstitial space. Such factors as fluid composition and pressure may be varied as desired in the perfusion circuits of the present device in order to simulate various conditions and flow rates.

It is thought that the invention and many of its attendant advantages will be understood from the foregoing description, and it will be apparent that various changes may be made in the apparatus and methods as described herein without departing from the spirit and scope of the invention or sacrificing its material advantages, the forms hereinbefore described being merely preferred embodiments thereof.

The concept of using different pressures in the two perfusion circuits to produce convection of the nutrient medium in the extracapillary space is intended to include both a difference in hydrostatic pressures in the individual perfusion circuits and osmotic pressures as would result from differential concentrations of poorly diffusing substances such as albumin within the perfusate media.

The embodiments of the invention in which an exclusive property or privilege is claimed are defined as follows:

1. A cell culture unit for the formation and maintenance of solid tissues and cells in vitro, comprising:
 (a) shell means having spaced end portions and defining an elongated chamber therebetween;
 (b) an endpiece attached to each end of said shell means, each endpiece terminating at its outer end in a plurality of tubular header members;
 (c) capillary means within said chamber, said capillary means including a plurality of individual capillaries having walls which are permeable to nutrients required for cell growth or maintenance and/or cell products and being arranged with individual capillaries extending in a predetermined reproducible interwoven relationship with respect to each other, said capillaries dividing the chamber by the walls of the capillaries into an intracapillary space within the capillaries and an extracapillary space outside the capillaries, the intracapillary space and the extracapillary space communicating with each other only through the walls of the capillaries, a first portion of said capillaries extending through a first header at each end of the shell means and a second portion of said capillaries extending through a second header at each end of the shell means, each portion being woven with the other such that capillaries from the separate portions are in intimate contact in a regular pattern;

(d) means communicating with the intracapillary space of said first portion of said capillaries for passing perfusate therethrough;

(e) means communicating with the intracapillary space of said second portion of said capillaries for passing perfusate therethrough; and (f) means communicating with said extracapillary space for seeding cells and/or retrieving cells or cell products therefrom.

2. In a cell culture unit for the formation and maintenance of solid tissues and cells in vitro including shell means having spaced end portions and defining an elongated chamber therebetween, a multiplicity of individual capillaries extending within said chamber from one end to the other and dividing the chamber by the walls of the capillaries into an intracapillary space within the capillaries and an extracapillary space outside the capillaries, the walls of the capillaries being permeable to nutrients required for cell growth or maintenance and/or cell products and the intracapillary space and the extracapillary space communicating with each other only through the walls of the capillaries, means communicating with the intracapillary space for passing perfusate therethrough, and means communicating with the extracapillary space for seeding of cells and/or retrieving cells or cell products therefrom, the improvement which comprises said capillaries being interwoven with respect to each other between the end portions of said chamber in a predetermined regular reproducible pattern such that the capillaries are in intimate contact with each other.

* * * * *